(12) United States Patent
Durrant

(10) Patent No.: US 10,295,443 B2
(45) Date of Patent: May 21, 2019

(54) HEMATOXYLIN PRECIPITATE CLEANING METHOD AND SYSTEM

(71) Applicant: Ventana Medical Systems, Inc., Tucson, AZ (US)

(72) Inventor: Edward E. Durrant, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 183 days.

(21) Appl. No.: 15/338,186

(22) Filed: Oct. 28, 2016

(65) Prior Publication Data

US 2017/0045429 A1 Feb. 16, 2017

Related U.S. Application Data

(63) Continuation of application No. PCT/EP2015/059075, filed on Apr. 27, 2015.

(60) Provisional application No. 61/986,386, filed on Apr. 30, 2014.

(51) Int. Cl.
| | |
|---|---|
| *G01N 1/00* | (2006.01) |
| *G01N 1/30* | (2006.01) |
| *G01N 1/31* | (2006.01) |
| *G01N 35/10* | (2006.01) |

(52) U.S. Cl.
CPC .............. *G01N 1/30* (2013.01); *G01N 1/31* (2013.01); *G01N 35/1002* (2013.01)

(58) Field of Classification Search
CPC ...................................................... G01N 1/00
See application file for complete search history.

(56) References Cited

U.S. PATENT DOCUMENTS

| | | |
|---|---|---|
| 2002/0034488 A1 | 3/2002 | Kravtchenko et al. |
| 2006/0105359 A1 | 5/2006 | Favuzzi et al. |
| 2013/0149790 A1 | 6/2013 | Mennicken et al. |

FOREIGN PATENT DOCUMENTS

| | | |
|---|---|---|
| CN | 1552558 A1 | 12/2004 |
| WO | 91/13336 A1 | 9/1991 |
| WO | 01/65266 A1 | 9/2001 |
| WO | 2005028663 A2 | 3/2005 |
| WO | 2007125023 A1 | 11/2007 |
| WO | 2009/124099 A1 | 10/2009 |
| WO | 2013071357 A2 | 5/2013 |

OTHER PUBLICATIONS

International Search Report and Written Opinion dated Jul. 3, 2015 in corresponding PCT Application No. PCT/EP2015/059075, 11 pages.
Song, X.-Y. et al., Color fastness of reactive dyestuffs and its affecting factors (IV), Dyeing and Finishing, (2006), pp. 40-44, vol. 14.

*Primary Examiner* — Jyoti Nagpaul
(74) *Attorney, Agent, or Firm* — Ventana Medical Systems, Inc.

(57) ABSTRACT

A process for removing hematoxylin precipitate from a surface of an automated hematoxylin stainer, systems adapted for performing such processes. The process and systems use a hematein precipitate removal solution having a pH in the range of between about 8.9 and 10.5 and including a liquid oxidizing component and alkaline component. The hematein precipitate removal solution is placed in contact with a surface of the automated hematoxylin stainer, thereby dissolving any hematein precipitate deposited thereon.

19 Claims, No Drawings

HEMATOXYLIN PRECIPITATE CLEANING METHOD AND SYSTEM

CROSS REFERENCE TO RELATED APPLICATIONS

This patent application is a continuation of International Patent Application No. PCT/EP2015/059075 filed Apr. 27, 2015, which claims priority to and the benefit of U.S. Provisional Application No. 61/986,386, filed Apr. 30, 2014. Each of the above patent applications is incorporated herein by reference as if set forth in its entirety.

FIELD OF THE INVENTION

The present invention relates to a process and reagent system for removing hematoxylin precipitate, and in particular to automated processes for the removal of hematoxylin precipitate from automated staining equipment utilizing said reagent system.

BACKGROUND OF THE INVENTION

Several histochemical staining protocols, including Hematoxylin and Eosin (H&E) staining and Papanicolaou (PAP) staining, rely on the dye hematoxylin to stain cytological and tissue samples. In particular, hematoxylin staining of cell nuclei is used by pathologists to detect the presence of malignant and/or metastatic cells in a tumor biopsy sample.

Hematoxylin is a naturally-occurring compound found in the red heartwood of trees of the genus *Hematoxylon*. Hematoxylin itself is colorless in aqueous solution and is not the active ingredient that stains tissue components. Rather, an oxidation product of hematoxylin, hematein, becomes the active staining component of a hematoxylin dye solution, particularly upon forming a complex with a mordant. Hematein is produced naturally through exposure to air and sunlight. The natural process is termed "ripening", and can take 3 or more months to provide a solution suitable for staining cells.

Automated staining procedures and systems use mechanical systems to deliver staining solutions to a biological sample. Standard hematein staining procedures utilized a premixed stock containing both the hematoxylin-hematein and a mordant. Precipitates form in these premixed stocks. This is not generally a problem for manual staining procedures, where slides are treated with the hematoxylin staining solution in a container, such as a glass container. However, precipitates are a problem for automated staining systems where the precipitate can foul or clog delivery lines and make cleaning or purging of the delivery lines difficult. These changes to hematoxylin and the precipitates in staining solutions can result in staining inconsistencies. For example, hematoxylin stain stocks containing mordant are often allowed to ripen for an extended period of time, allowing developing of hematein-mordant complexes. While this process may allow for good staining results, it also results in formation of the undesirable precipitate.

An automated H&E staining instrument consists of many parts having substantial cost. Hematein precipitate buildup on surfaces of tubing, valves, dispense manifolds, etc. can have impacts ranging from on-slide precipitate to interference or occlusion of hematoxylin dispense. Precipitation is also exacerbated by contact with metal. This is especially problematic for automated systems which contain metal parts such as nozzles and spray heads with very small diameter openings which can be clogged by precipitates. In the case of on-the-slide precipitate, the impact can be as low as being a nuisance for the pathologist reading the slide, to as high as impacting diagnostic utility. Substantial buildup of precipitate in the staining module can require the replacement of parts, or in the worst case, replacement of an entire staining module to remediate this issue.

The problem of precipitate can be solved through the use of a cleaning solution of some kind that dissolves the precipitate. The chemical makeup and physical properties of the cleaning solution must be tailored to the design of the staining module, such that the solution is compatible with the materials that comprise the various parts of the module. Additional considerations such as corrosiveness and health/safety hazards must be kept in mind from both a manufacturing and customer use point of view.

Traditional cleaning solutions for the removal of hematoxylin precipitate are generally modeled on 'acid alcohol', whose composition comprises a low percentage of hydrochloric acid (1-2%) in an ethanol-water mixture (typically 70% ethanol, 30% water). A solution comprised of hydrochloric acid (~1%) in a mixture of propylene glycol and water was found to dissolve the precipitate formed from hematoxylin. The solubility of the precipitate in this solution was determined to be ~15 milligrams/milliliter, and the dissolution rate in the absence of active mixing was quite low (empirical observation). In actual experiments with this cleaner, the contact time of the cleaner with the interior parts of the staining module may need to be on the order of days in order to effect total removal of precipitate. As a preventative maintenance cleaning solution for a staining instrument or module, the slow rate of dissolution of the precipitate by this traditional cleaner is unacceptably long. A stronger concentration of hydrochloric acid would improve both the rate of dissolution and the total solubility at the expense of being a more corrosive and hazardous material.

The use of chlorine bleach (sodium hypochlorite) to remove hematoxylin stains from affected surfaces has also been known. These bleach solutions are corrosive, however, and they can be a nuisance and a potential safety hazard to work with as they often discolor clothing and other textiles. Additionally, many people are sensitive to the chlorine fumes that emanate from these solutions.

A better solution to this issue would be in the use of a more efficacious formulation that is able to dissolve the precipitate to a higher extent and at a faster rate. Therefore, a need exists for development of a hematoxylin/hematein precipitate cleaning system and procedures that are compatible with internal storage containers, delivery lines and nozzles of automated sample processing instruments.

It is known that hydrogen peroxide is a strong oxidizer of odor causing molecules in textiles. During the treatment of affected odorous textiles hydrogen peroxide oxidizes the odorous precipitate molecules into non-malprecipitateous compounds. For example, pet urine precipitate molecules may be oxidized and rendered non-malprecipitateous. The treatment process is often combined with a cleaning device such as a vacuum cleaner. Since an aqueous solution of hydrogen peroxide is relatively stable at room temperature and hydrogen peroxide will not substantially decompose into oxygen and water unless activated, the textile odor removal process provides a buffering agent to activate the hydrogen peroxide once the two agents are mixed. In the known textile odor removal treatment the liquid buffering agent is often sodium carbonate.

Overview of the Technology

One embodiment is a method for removing hematein precipitate from internal storage containers, delivery lines, nozzles, and other reagent delivery components of automated hematoxylin staining apparatus. This can be achieved by combining a liquid oxidizing component comprising a peroxide and water and an alkaline component in a container to form a hematein precipitate removal solution having a pH in the range of between about 8.9 and 10.5. I.e., the liquid oxidizing component and the alkaline component are provided as separate components before combining them in a container. The container is then placed in a position to enable the hematoxylin dispensing components of an automated hematoxylin staining system to receive and move the solution through the interior surfaces of those dispensing components. The automated staining system is activated to move the precipitate removal solution into the interior surfaces of the hematoxylin dispensing components of the automated staining system were the interior surfaces are in contact with the precipitate removal system for at least 30 minutes.

Another embodiment relates to a precipitate removal system that includes a liquid oxidizing component comprising a peroxide and water; and a liquid alkaline component comprising a sodium citrate and water, wherein the liquid oxidizing component and the liquid alkaline component are combinable to form a solution having a pH from prior to contacting the hematein precipitate.

DETAILED DESCRIPTION

Automated slide staining apparatus increase the consistency and controllability of certain attributes (e.g., stain intensity) of histologically processed specimens. Processing time (i.e., the duration of a given histological process) and processing temperature (i.e., the temperature at which a given histological process is carried out) are two variables that affect most, if not all, of these attributes. Automated histological systems generally include features that facilitate consistency and/or controllability of processing time and/or processing temperature. For example, at least some of these systems include stainer apparatus having processing heads capable of executing precisely controlled liquid dispensing and removing operations. These stainers can also have internal environments that can be maintained at elevated baseline temperatures. The performance (e.g., with respect to quality and/or versatility) of these and other automated systems so configured far exceed that of conventional, automated "dip and dunk" apparatus.

Hematoxylin solutions used for diagnostic tissue staining often suffer from the formation of undesirable precipitates. In an anatomical pathology laboratory that performs automated linear (dip n' dunk) or manual staining, the precipitate can be controlled from interfering with the staining process by simply filtering the precipitate from the solution and reusing the filtrate for staining or replacing the old solution with new solution. Any precipitate on the surfaces of the container used to hold the solution can be addressed by chemical cleaning, or by simply replacing the container with a new one.

Within the confines of an automated H&E staining instrument there are many parts. Many parts can have substantial cost. Hematoxylin precipitate buildup on surfaces of tubing, valves, dispense manifolds, etc., can have impacts ranging from on-slide precipitate to interference or occlusion of hematoxylin dispense. In the case of on-slide precipitate, the impact can be as low as being a nuisance to as high as impacting diagnostic utility. Substantial buildup of precipitate in the staining module can require the replacement of parts, or in the worst case, replacement of the entire module to remediate this issue. This problem can be solved through the use of a cleaning solution of some kind that dissolves the precipitate.

The chemical makeup and physical properties of this cleaning solution must be tailored to the design of the staining module, such that the solution is compatible with the materials that comprise the various parts of the module. Additional considerations such as corrosiveness and health/safety hazards must be kept in mind from both a manufacturing and customer use point of view.

The precipitate removal treatment system of the invention comprises a liquid oxidizing component comprising a peroxide and water; and an alkaline component, wherein the liquid oxidizing component is stored separately from the complexing component. Each component of the precipitate removal system is combined to form a solution having a pH from 9.5 to 10 prior to contacting the hematein precipitate. Generally, the liquid oxidizing and the alkaline component are combined/mixed in a container to form a precipitate removal solution. The precipitate removal solution container can be a container that will fit into a reagent receiving position on the automated stainer or the container can be a stand-alone container. If the container is a stand-alone container there will need to be hoses, tubing or other fluid transport means to allow the precipitate removal solution access to the interior surfaces of the stainer's fluid dispensing apparatus. Once the precipitate removal solution has been prepared it will replace the hematoxylin reagent throughout the automated stainer's fluid dispensing apparatus and is thereafter allowed to remain in contact with the interior fluid path of the reagent delivery components for at least 30 minutes. The precipitate removal solution can also be pumped (pressure) or pulled (vacuum) throughout the internal surfaces of the automated staining system's reagent dispensing apparatus until the solution container has been emptied. The staining dispensing apparatus is then purged of the precipitate removal solution and refilled or primed with the automated system's standard staining reagent(s).

EXAMPLES

Spotting Test Experiment

A six month old, unopened bottle of a hematoxylin solution (<1% hematoxylin dye, <4% aluminum sulfate, <0.1% sodium iodate, <1% hydroquinone, and <2% beta-cyclodextrinhydrate in a glycol stabilizing solution) was obtained. The solution was drained from the bottle and the bottle was rinsed three times with DI water. There was a noticeable precipitate residue on the inside of the bottle where the hematoxylin solution contacted the inside of the bottle. The bottle was cut open and the DI water residue was allowed to evaporate. Portions of the bottle that contained the precipitate residue were obtained and used in the spotting test.

A portion of the cut away bottle was laid on the lab bench with the inner side of the bottle portion facing up. This inner side is the side of the bottle portion that is coated with precipitate residue. One drop of test cleaning solution is placed on the bottle portion and is allowed to remain for 15 seconds. After 15 seconds, the test cleaning solution is rinsed away with DI water and the spot is examined visually for evidence of precipitate removal.

Tubing Loop Experiment

A 12 inch section of Perfluoroalkoxy polymer (PFA) tubing is filled with an aqueous hematoxylin solution [25% ethylene glycol (v/v), 20 mM hematoxylin, 3.3 mM sodium iodate, 20 mM aluminum sulfate octadecahydrate, 85 mM hydroquinone and 10 mM β-cyclodextrin 60 hydrate having a pH of about 2.5]. The tubing was joined at both ends with a coupler to form a loop. The tubing loop was placed in an oven held at 60° C. for about 14 days. During this time, the heat causes the hematein to precipitate and coat the inside of the tubing loop. After the heated incubation period, the tubing loop was removed, drained, and rinsed with DI water. The loop was then left open and allowed to dry. This left tubing with a dark coating of hematein precipitate coating the inside wall of the tubing.

To test a cleaning solution, a pre-precipitated tubing loop was filled with a test cleaning solution, closed to form a loop, and allowed to sit for about 1 minute at room temperature. The solution was then drained and the tubing was rinsed with DI water. The tubing was then examined visually for evidence of precipitate removal.

Experiment 1

A spot test experiment using a 1:1 mixture of 3% hydrogen peroxide solution and 0.5M sodium carbonate solution showed excellent cleaning results.

Experiment 2

A tubing loop experiment comparing a 0.125M iron(III) chloride solution, a 1M phosphate buffer (pH=2), a 0.64M phosphoric acid solution, a 0.1M hydrochloric acid in 50% propylene glycol, and a 3% hydrogen peroxide-50 g/L sodium carbonate solution was conducted. The 3% hydrogen peroxide-50 g/L sodium carbonate solution cleaned the tube completely. The other solutions all left precipitate residue on the tubing walls.

Experiment 3

A spot test experiment was conducted comparing different 2-part peroxide solutions. The experimental set-up and results are shown in Table 1.

TABLE 1

| Solution | pH | Cleaning Results |
|---|---|---|
| 100 mL of 3% hydrogen peroxide + 1 g of TRIS | 9.2 | Poor. Some cleaning observed |
| 100 mL of 3% hydrogen peroxide + 40 mL of 0.1M KOH | 9.8 | Decent/good |
| 100 mL of 3% hydrogen peroxide + 1 g of sodium carbonate | 9.85 | Decent/good |
| 100 mL of 3% hydrogen peroxide + 2 g of sodium carbonate | 9.9 | Good |
| 100 mL of 3% hydrogen peroxide + 3 g of sodium carbonate | 10 | Excellent |
| 100 mL of 3% hydrogen peroxide + 5 g of sodium carbonate | 10 | Excellent |

Experiment 4

A spot test experiment comparing a 0.2M oxalic acid solution, a 0.2M sodium sulfite solution, a 0.2M potassium disulfite solution, and a 1M sodium persulfate-10 g/L sodium carbonate solution was conducted. The 1M sodium persulfate-10 g/L sodium carbonate solution and the 0.2M oxalic acid solution exhibited excellent cleaning results. The other solutions showed no cleaning ability.

Experiment 5

A modified tubing loop experiment (60 minute cleaning soak) was conducted with varying strengths of sodium persulfate mixed 1:1 with a sodium carbonate solution. The experimental set-up and results are shown in Table 2.

TABLE 2

| Solution part 1 | Solution part 2 | Results |
|---|---|---|
| 0.5M sodium persulfate | 60 g/L sodium carbonate | Complete removal of precipitate residue |
| 0.25M sodium persulfate | 60 g/L sodium carbonate | Complete removal of precipitate residue |
| 0.1M sodium persulfate | 60 g/L sodium carbonate | Complete removal of precipitate residue |

Experiment 6

A tubing loop experiment was conducted with alternate bases used to elevate the pH of a hydrogen peroxide solution. The experimental set-up and results are shown in Table 3. The mixture of carbonate and phosphate as a base seemed to perform better than just carbonate by itself.

TABLE 3

| Solution part 1 | Part 2 | pH | Results |
|---|---|---|---|
| 100 mL of 3% hydrogen peroxide solution | 1 mL ethanolamine | 10.0 | Precipitate removed from tubing wall. Precipitate solids left undissolved for hours. |
| 100 mL of 3% hydrogen peroxide solution | 2 g of trisodium phosphate dodecahydrate | 10.15 | Precipitate removed from tubing wall. Precipitate solids left undissolved for 3 to 5 minutes. |
| 100 mL of 3% hydrogen peroxide solution | 3 g of sodium glycine monohydrate | 10.19 | Precipitate removed from tubing wall. Precipitate solids left undissolved for 3 to 5 minutes. |
| 100 mL of 3% hydrogen peroxide solution | 2 g of sodium carbonate & 1 g of trisodium phosphate dodecahydrate | 10.16 | Precipitate removed from tubing wall. Precipitate solids left undissolved for about 1 minute. |

The invention claimed is:

1. A method of removing hematein precipitate from an automated hematoxylin staining system comprising:
   providing a liquid oxidizing component comprising a peroxide and water and an alkaline component, wherein the liquid oxidizing component and the alkaline component are separate;
   combining the liquid oxidizing component and alkaline component in a container to form a hematein precipitate removal solution having a pH in the range of between about 8.9 and 10.5;
   placing the container of the hematein precipitate removal solution in a position to enable one or more hematoxylin dispensing component(s) of the automated hematoxylin staining system to receive and move the solution through an interior surface of the one or more hematoxylin dispensing component(s);
   activating the automated staining system to move the hematein precipitate removal solution into the interior surface of the hematoxylin dispensing component(s);
   contacting said interior surface for at least 30 minutes.

2. The method of claim 1, wherein the peroxide is hydrogen peroxide.

3. The method of claim 2, wherein the solution has a hydrogen peroxide weight percent in the range of from 1% to less than 8%.

4. The method of claim 2, wherein the solution has a hydrogen peroxide weight percent in the range of between about 3% and 7%.

5. The method of claim 2, wherein the solution has a hydrogen peroxide weight percent of about 6%.

6. The method of claim 1, wherein the solution has a pH in the range of between about 9.5 and 10.5.

7. The method of claim 1, wherein the solution has a pH of about 10.

8. The method of claim 1, wherein the alkaline component comprises an alkaline agent selected from the group consisting of sodium carbonate, sodium glycine and trisodium phosphate.

9. The method of claim 8, wherein the alkaline component is in liquid form and further comprises water.

10. The method of claim 1, wherein the removal solution container is configured as a staining reagent container for the automated hematoxylin staining system to be cleaned.

11. The method of claim 10, wherein the removal solution container comprises keying features to allow substitution of a reagent container on the automated hematoxylin staining system to enable the hematoxylin dispensing components of the automated hematoxylin staining system to receive and move the solution through the interior surfaces of those dispensing components.

12. The method of claim 1, wherein the method further comprises removing the precipitate removal solution from the interior surfaces of the automated dispensing components and replacing said precipitate removal solution with a staining reagent by further activation of automated staining system.

13. A method of removing a hematein precipitate from a surface of an automated hematoxylin staining system comprising contacting said surface with a hematein precipitate removal solution having a pH in the range of 8.9 to 10.5 for a period of time sufficient to dissolve the hematein precipitate, wherein said hematein precipitate removal solution comprises an aqueous peroxide solution combined with an alkaline component.

14. The method of claim 13, wherein the peroxide is hydrogen peroxide.

15. The method of claim 14, wherein the solution has a hydrogen peroxide weight percent in the range of from 1% to less than 8%.

16. The method of claim 13, wherein the alkaline component comprises an alkaline agent selected from the group consisting of sodium carbonate, sodium glycine and trisodium phosphate.

17. The method of claim 13, wherein said surface is an interior surface of a hematoxylin dispensing component of the automated hematoxylin staining system.

18. An automated hematoxylin staining system comprising:
  (a) a hematoxylin dispensing component having a surface susceptible to hematein precipitate buildup; and
  (b) a source of a hematein precipitate removal solution having a pH in the range of 8.9 to 10.5, said hematein precipitate removal solution comprising an aqueous peroxide solution combined with an alkaline component;

wherein said automated slide stainer is configured to move the hematein precipitate removal solution in contact with the interior surface of the hematoxylin dispensing component for a sufficient period of time to dissolve the hematein precipitate buildup.

19. The automated hematoxylin staining system of claim 18, wherein the hematoxylin dispensing component includes at least one of tubing, a valve, and a dispense manifold.

* * * * *